United States Patent [19]

Gelb

[11] Patent Number: 5,538,424
[45] Date of Patent: Jul. 23, 1996

[54] RADIOGRAPHIC DEPTH AND PROSTHETIC POSITIONING GUIDE

[76] Inventor: David A. Gelb, 836 Farmington Ave., Suite 131, West Hartford, Conn. 06119

[21] Appl. No.: 280,942

[22] Filed: Jul. 27, 1994

Related U.S. Application Data

[63] Continuation of Ser. No. 245,735, May 18, 1994, abandoned.

[51] Int. Cl.⁶ .............................. A61C 19/04; A61C 8/00
[52] U.S. Cl. ........................... 433/72; 433/173; 378/163
[58] Field of Search .......................... 433/72, 76, 173, 433/174; 378/163, 170, 204, 205

[56] References Cited

U.S. PATENT DOCUMENTS

| | | | |
|---|---|---|---|
| D. 296,362 | 6/1988 | Branemark | D24/33 |
| D. 317,200 | 5/1991 | Jorneus | D24/156 |
| D. 319,500 | 8/1991 | Soderberg | D24/156 |
| 3,726,011 | 4/1973 | Savignano | |
| 4,005,527 | 2/1977 | Wilson et al. | 33/111 |
| 4,016,651 | 4/1977 | Kawahara et al. | |
| 4,185,383 | 1/1980 | Heimke et al. | 433/173 |
| 4,215,986 | 8/1980 | Riess | 433/173 |
| 4,279,252 | 7/1981 | Martin | 128/349 R |
| 4,416,629 | 11/1983 | Mozsary et al. | 433/174 |
| 4,431,416 | 2/1984 | Niznick | 433/174 |
| 4,531,915 | 7/1985 | Tatum, Jr. | 433/173 |
| 4,547,156 | 10/1985 | Hader | 433/172 |
| 4,552,532 | 11/1985 | Mozsary | 433/173 |
| 4,713,003 | 12/1987 | Symington et al. | 433/173 |
| 4,722,688 | 2/1988 | Lonca | 433/173 |
| 4,756,689 | 7/1988 | Lundgren et al. | 433/173 |
| 4,850,870 | 7/1989 | Lazzara et al. | 433/174 |
| 4,854,872 | 8/1989 | Detsch | 433/174 X |
| 5,030,096 | 7/1991 | Hurson et al. | 433/141 X |
| 5,183,414 | 2/1993 | Czerniawski | 433/76 |
| 5,208,845 | 5/1993 | Gelb | 378/163 |
| 5,320,529 | 6/1994 | Pompa | 433/76 |

FOREIGN PATENT DOCUMENTS

| | | |
|---|---|---|
| 3531389 | 3/1985 | Germany . |
| 8502337 | 6/1985 | Sweden . |
| 2176709 | 1/1987 | United Kingdom . |
| WO94/09719 | 5/1994 | WIPO . |
| WO94/21190 | 9/1994 | WIPO . |

Primary Examiner—Nicholas D. Lucchesi
Attorney, Agent, or Firm—Welsh & Katz, Ltd.

[57] ABSTRACT

A radiographic guide for accurately positioning a proposed implant in the jawbone of a patient. The guide has a lower rod portion configured to fit within a pilot bore drilled in the jawbone and an upper cap configured to correspond to the shape and dimensions of a commercially available implant. The rod portion may include depth markings to indicate distances from a selected reference point. Placing a guide into the pilot bore, visually inspecting the cap of the guide, and taking an x-ray using a method to give anatomically correct distances gives an indication of the appearance, probable position and angulation of the proposed implant prior to the implantation of the implant into the jawbone.

6 Claims, 1 Drawing Sheet

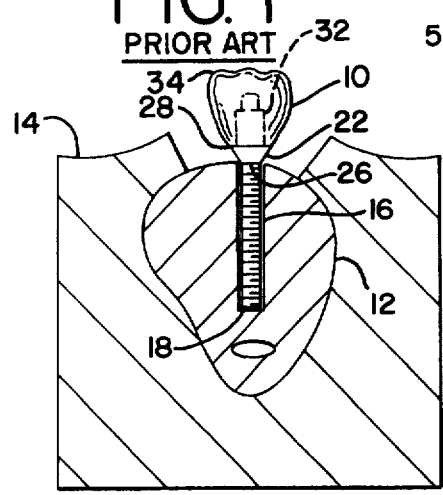
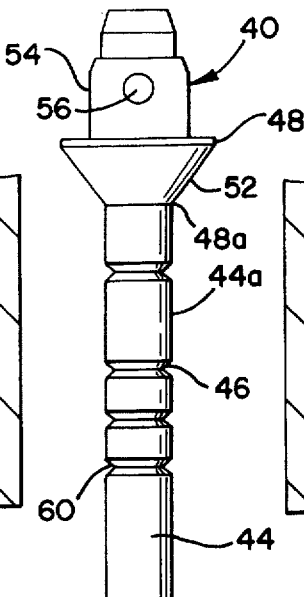
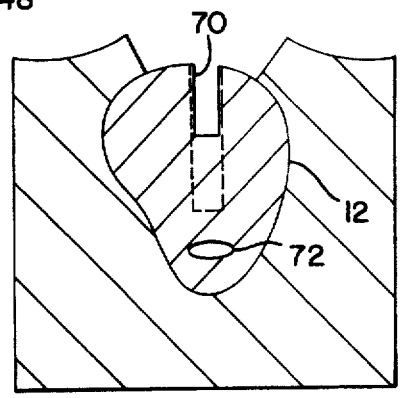
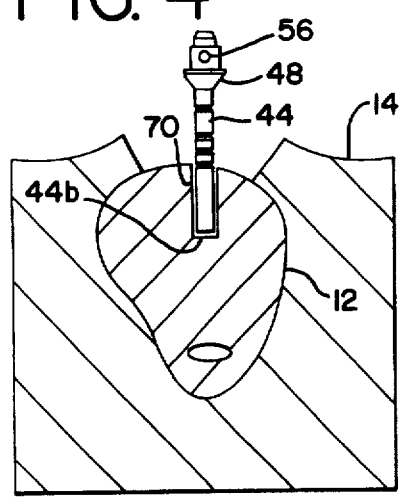
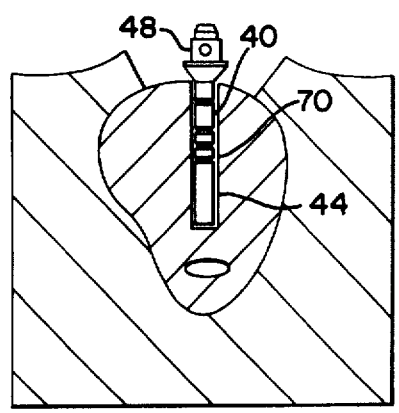
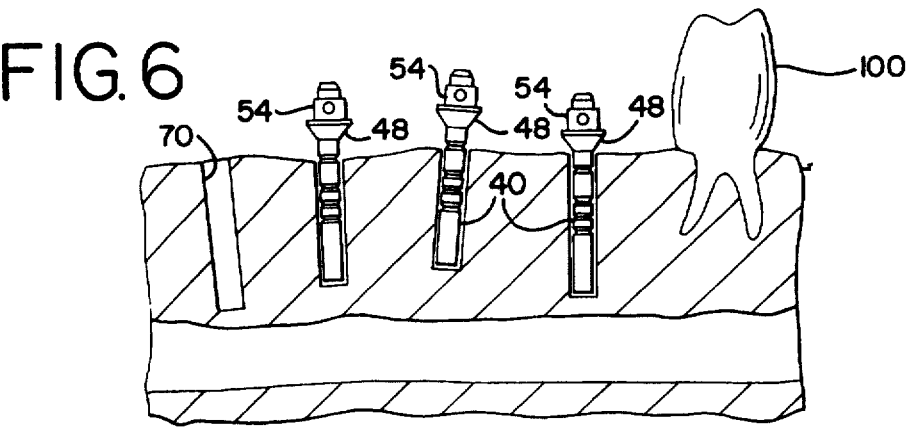

RADIOGRAPHIC DEPTH AND PROSTHETIC POSITIONING GUIDE

This is a continuation of application Ser. No. 08/245,735 filed May 18, 1994, now abandoned.

BACKGROUND OF THE INVENTION

This invention relates generally to a guide for use during the process of the installation of dental prosthetic implants. More particularly, the invention includes a positioning and depth guide for determining the appearance, relative position and alignment of a dental implant prior to its insertion into a jaw.

The field of prosthodontics restoration, whereby an object substituting for a natural tooth and tooth root is surgically implanted in the jaw, has come into increasingly wide use. In prosthodontics restoration, a dental implant is implanted in the gum tissue and jaw bone of a patient. In the typical dental implant process, a titanium post or fixture is press fitted or screwed into a hole drilled into the jaw bone. The fleshy gum tissue is then sutured to cover the fixture and the fixture remains in the hole until osseointegration takes place to firmly fix the post to the jaw bone. After a sufficient time has past for osseointegration, the gum tissue is opened to expose an upper end of the fixture. A restoration supporting abutment is then secured to the fixture and a restoration such as a tooth is then affixed to the abutment.

It is important that the fixture is structurally anchored to the jaw bone. To provide the proper structural support, the lower end of the fixture should penetrate for a desired depth into the jaw bone, however, the fixture should not damage other structures in the jaw bone and surrounding areas such as nerves and sinuses. As set forth in U.S. Pat. No. 5,208,845 and incorporated herein by reference, one method of ascertaining the correct placement of a new fixture in the gums and jaw bone is to drill progressively deeper bores for the fixture, and insert radiographic guides which through the use of x-rays indicate the depth and singulation of the bores.

However the radiographic gages often do not give an accurate representation of the appearance of the abutment. And, although the radiographic gages provide a good gauge of the depth and singulation of the implant bore, the guides provide little guidance in selecting the proper height of the abutment for the contemplated implant.

Therefore, an object of the present invention to provide an improved device for indicating the positioning of a prosthetic device such as a dental implant.

A further object of the present invention to provide an improved guide for radiographically determining the probable orientation and position of an abutment portion of a dental implant.

A still a further object of the present invention is to provide an improved radiographic guide for determining the proper height and angulation of an abutment of an implant.

An additional object of the present invention is to provide a guide which may be used with standard x-ray techniques.

SUMMARY OF THE INVENTION

The above objects are met and exceeded by a radiographic guide for selecting and accurately positioning a dental implant prior to the implantation in the jaw bone of a patient. The guide has a lower rod portion configured to fit within a pilot bore drilled in the jawbone and an upper cap configured to correspond to the shape and dimensions of a commercially available implant. The rod portion may include depth markings to indicate distances from a selected reference point. Placing a guide into the pilot bore and taking an x-ray using a method to give anatomically correct distances shows the probable position and angulation of the proposed implant prior to the implantation of the implant into the jawbone. Visual inspection of the cap of the guide provides an accurate representation of the appearance of the implanted abutment.

BRIEF DESCRIPTION OF THE DRAWINGS

FIG. 1 is a cross sectional view of a jawbone showing a BRANEMARK SYSTEM® implant and tooth restoration device;

FIG. 2 is a side view of a radiographic dental prosthetic alignment and placement guide according to the present invention;

FIG. 3 is a cross sectional view of a lower jawbone showing a pilot hole relative to an anatomical structure such as the illustrated nerve canal;

FIG. 4 is the jawbone of FIG. 3 with the guide of FIG. 2 inserted into the pilot hole;

FIG. 5 is a view of the jawbone of FIG. 4 with the cap, forming a part of the guide, contacting the jawbone;

FIG. 6 is a side sectional view of a length of jawbone having a multiplicity of pilot holes with inserted guides.

DESCRIPTION OF THE PREFERRED EMBODIMENTS

Referring to FIG. 1, a dental implant 10 is shown installed in a jaw bone 12 covered with gum tissue 14. The implant 10 includes a threaded fixture 16 which extends into a bore 18 which has been fashioned in the gum tissue 14 and jaw bone 12. In a typical implant procedure, gum tissue 14 is opened to expose the jawbone 12 and the bore is drilled in the jawbone. The fixture 16 is then threaded or force fitted in the bore 18 and the gum tissue 14 is sutured to close over the fixture. After a period of time, the jawbone 12 attaches to the fixture 16 through osseointegration.

After osseointegration, an abutment post 22 is engaged to an upper end of the fixture 16. In FIG. 1, the fixture 16 and abutment 22 shown, is one of several different types of implant, the BRANEMARK SYSTEM® implant. In a BRANEMARK SYSTEM® implant, the abutment 22 has a frustoconical lower portion having a narrow lower end 26 and a relatively wider upper end 28.

Extending upward from the upper end 28 of the abutment 22 is a cylindrical upper portion or mount 32 for attaching an artificial tooth such as the illustrated crown 34. The attachment is preferably made by a threaded engagement between the crown 34 and the mount 32. As may be noted in the figure, one of determining factors of the height of the crown 34 relative to the surrounding teeth is the height of the abutment 22.

Referring to FIG. 2, a preferred embodiment of the present radiographic dental prosthetic guide according to the present invention is indicated generally at 40. The guide 40 is composed of a material which shows clearly on an x-ray such as stainless steel or the like. The guide 40 includes a lower rod 44 having depth markings, indicated at 46, placed at predetermined locations along the length of the rod. The rod 44 preferably has a smooth cylindrical outer surface.

Attached to the upper end 44a of the rod 44 is a cap 48 which is configured to give the appearance of the abutment 22 shown in FIG. 1 for purposes of illustration of the present implantation. It is apparent that for implants 10 having abutments 22 or mounts 32 or similarly functioning elements of differing configurations, the cap 48 will be configured and dimensioned in a different manner. It is also apparent that even for a particular type of implant 10, the height of the cap 48 may be selectively varied to reflect the different heights of abutments 22 which may be used in a particular application.

To reflect the configuration of the BRANEMARK SYSTEM® implant 10, the cap 48 has a lower frusto-conical section 52 and an upper cylindrical section 54 which extends upward from the top of the lower section 52. A hole 56 extends through the upper section 54, preferably horizontally, to provide a passageway for thread, floss (not shown) or the like. The floss may be used to remove the guide 40 from the mouth of the patient and also used as a safety measure to prevent the guide from inadvertently going into the patient's throat or windpipe.

In the preferred embodiment, the depth markings 46 are provided by reducing the diameter of the rod 44 to form bands 60. The bands 60 should be dimensioned so that the bands are visible on an x-ray. The position of each of the bands 60 along the rod 44, and particularly from a desired reference point such as the bottom end 44b of the rod, is selected to correspond to potential implant lengths. For example, BRANEMARK SYSTEM® implants 10 may be found in lengths of 7, 10, 13, 15, 18 and 20 millimeters ("mm"). Thus, the guide 40 may have one or more bands 60 located at a distance from the bottom end 44b corresponding to these BRANEMARK SYSTEM® lengths. For example, the guide 40 may have two bands 60 located at distances of 7 mm and 10 mm from the bottom end 44b. It is also preferred that the bottom edge 48a of the cap 48 also functions as a depth marker 46.

Referring to FIG. 3, in use, after the jawbone 12 is exposed, a pilot hole 70 is drilled in the jawbone. The diameter of the hole 70 should correspond to the diameter of the rod 44 of the guide 40. The diameters of both the rod 44 and the hole 70 should be less than the bore 18 (FIG. 1) for the actual implant 10 so that the angulation of the drilled hole 70 may be corrected.

Referring to FIG. 4, a floss (not shown) may be threaded through the hole 56 of the guide 40 as a safety measure to reduce the chance that the guide may travel inadvertently into the patient's windpipe or throat. The rod 44 of the guide 40 is then inserted in the hole 70 until the bottom 44b of the rod contacts the bottom of the hole.

The appearance of the cap 48 may be visually inspected to provide an indication of the appearance of the abutment 22. An x-ray is then taken of the inserted guide 40. It is preferred that the dimensions shown on the x-ray be equivalent to the actual dimensions of the jawbone 12 and guide 40. Thus by examining the x-ray, the depth markings 46 of the guide 40 indicate the depth of the hole 70 and the position of the guide and hole may be checked relative to surrounding structures such as a nerve 72.

During some processes of taking an x-ray, the length of the guide 40 may be important to the process. For example, the Rinn Bite Block System typically requires that the teeth be clenched together to hold the film container. Therefore, the guide 40 selected should have a total length such that when the guide is inserted into the hole 70, the top of the upper section 54 is below the top of the teeth 100 as shown in FIG. 6, so that the teeth may still be clenched together.

The x-ray also reveals the angulation of the guide 40 and therefore the hole 70. From the examination of the x-ray, adjustments may be made in the depth and angulation of the hole 70. In addition, using the x-ray as a guide, adjacent teeth may be marked to assist in drilling at the desired angulation.

Because the cap 48 is dimensioned similar to the abutment 22, it is apparent that the visual inspection and x-ray of the cap of the inserted guide 40 also gives an indication of what will be the position and alignment of the implanted abutment 22. If the depth and angulation of the pilot hole 70 are satisfactory and the appearance and position of the cap 48 is satisfactory, the implantation of the fixture 16 may begin.

If the position, angulation or appearance of the guide 40 is unsatisfactory, additional drilling may be undertaken or a second guide 40 having a different configured cap 48 may be inserted in the pilot hole 70. For example, the hole 70 may be drilled to a depth which corresponds to an implant length, provides the desired penetration into the jawbone 12 for structural requirements, and does not damage surrounding structures.

Referring to FIG. 5, once the desired depth is achieved, a guide 40 with a rod 44 of a length corresponding to the depth of the hole 70 is inserted into the hole. If more than one bore 18 is needed for a desired implant, multiple holes 70 and inserted guides 40 may be constructed, as shown in FIG. 6.

An x-ray may then be taken of the guides 40 which accurately represents what the angulation and position of the implants 10 will be when implanted into the jawbone 12. Corrections may be made if the x-ray reveals undesired angulation and positioning.

The caps 48 of the inserted guides 40 may be visually inspected as representative of the appearance of the implanted abutment 22. Also, as noted above, guides 40 having caps 48 of differing heights may be inserted into the holes 70 and visually inspected to determine the properly configured abutment 22 (FIG. 1) so that the dental prosthesis will be cosmetically similar to the surrounding teeth. Tweezers (not shown) or the like may then be used to remove the guides 40 by gripping the caps 48.

Referring to FIGS. 1 and 5, thus the guide 40 permits precise placement of implants 10 in a jawbone 12 so that osseointegration may take place while reducing the potential for damage to surrounding structures. Also use of caps 48 which closely resemble the abutments 22 of the proposed implant 10 increases the likelihood that once the implants 10 are implanted and the artificial teeth are affixed to the implants, the artificial teeth or other dental prosthetic fixture will be of the desired height and angulation.

A specific embodiment of the novel radiographic depth & prosthetic positioning guide according to the present invention has been described for the purposes of illustrating the manner in which the invention may be made and used. It should be understood that implementation of other variations and modifications of the invention in its various aspects will be apparent to those skilled in the art, and that the invention is not limited by the specific embodiment described. It is therefore contemplated to cover by the present invention any and all modifications, variations, or equivalents that fall within the true spirit and scope of the basic underlying principles disclosed and claimed herein.

What is claimed is:

1. A radiographic guide for accurately positioning a dental implant prior to the implantation of the implant in the jawbone of a patient, the implant including a fixture extending into a final bore drilled into the jawbone and an abutment attached to the fixture, the guide comprising:

an elongated rod having a diameter adapted to be substantially equal to the diameter of a pilot bore drilled in the jawbone, said pilot bore having a diameter less than the diameter of the final bore; and a cap integrally connected to one end of said rod, said cap comprising means for corresponding to the shape of the abutment; said rod includes at least one depth indicating means which is visually apparent on an x-ray, for indicating distances along said rod from a selected reference point.

2. The guide of claim 1 wherein the length of said rod corresponds to the length of the fixture.

3. The guide of claim 1 wherein said rod has a cylindrical surface.

4. A method for positioning a dental implant in a jawbone at a selected depth, the implant having an abutment configured to contact a jawbone and retain a dental prosthetic comprising;

drilling at least two pilot holes in the jawbone of a selected diameter deeper than the selected depth and inserting into said pilot holes a lower portion of both a first radiographic guide and a second radiographic guide having a cap configured similar to the abutment of the implant; and visually inspecting said inserted first and second guides; and taking an x-ray of the inserted first and second guides to determine the angulation of the pilot hole and location of the pilot hole relative to anatomical structures within the jawbone.

5. The method of claim 4 wherein said inserting step includes-contacting the upper cap with the jawbone.

6. The method of claim 4 further including evaluating the x-ray to determine if the pilot hole is at a desired depth and angulation and to determine the probable positioning and alignment of the abutment of the implanted implant.

* * * * *